(12) United States Patent
Soper et al.

(10) Patent No.: US 10,373,719 B2
(45) Date of Patent: Aug. 6, 2019

(54) SYSTEMS AND METHODS FOR PRE-OPERATIVE MODELING

(71) Applicant: Intuitive Surgical Operations, Inc., Sunnyvale, CA (US)

(72) Inventors: Timothy D. Soper, Sunnyvale, CA (US); Tao Zhao, Sunnyvale, CA (US); Caitlin Q. Donhowe, Mountain View, CA (US); Vincent Duindam, San Francisco, CA (US); Federico Barbagli, San Francisco, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 865 days.

(21) Appl. No.: 14/845,031

(22) Filed: Sep. 3, 2015

(65) Prior Publication Data
US 2016/0070878 A1 Mar. 10, 2016

Related U.S. Application Data

(60) Provisional application No. 62/048,595, filed on Sep. 10, 2014.

(51) Int. Cl.
*G16H 50/50* (2018.01)
*A61B 34/10* (2016.01)
*A61B 34/00* (2016.01)

(52) U.S. Cl.
CPC ............. *G16H 50/50* (2018.01); *A61B 34/10* (2016.02); *A61B 2034/105* (2016.02); *A61B 2034/252* (2016.02)

(58) Field of Classification Search
None
See application file for complete search history.

(56) References Cited

U.S. PATENT DOCUMENTS

| 6,380,732 | B1 | 4/2002 | Gilboa |
| 6,389,187 | B1 | 5/2002 | Greenaway et al. |
| 7,316,681 | B2 | 1/2008 | Madhani et al. |
| 7,930,065 | B2 | 4/2011 | Larkin et al. |
| 8,548,778 | B1 * | 10/2013 | Hart ........................ G06T 19/20 703/6 |

(Continued)

FOREIGN PATENT DOCUMENTS

WO WO-2015119935 A1 8/2015

OTHER PUBLICATIONS

Kaftan, Jens N., Atilla P. Kiraly, Annemarie Bakai, Marco Das, Carol L. Novak, and Til Aach. "Fuzzy pulmonary vessel segmentation in contrast enhanced CT data." In Medical Imaging 2008: Image Processing, vol. 6914, p. 69141Q. International Society for Optics and Photonics, 2008. (Year: 2008).*

(Continued)

*Primary Examiner* — Xiao M Wu
*Assistant Examiner* — Steven Z Elbinger
(74) *Attorney, Agent, or Firm* — Haynes & Boone, LLP

(57) ABSTRACT

A method for modeling a patient anatomy includes applying a first modeling function to a set of volumetric image data for a patient anatomy to produce a first model of the patient anatomy, presenting the first model to a user, receiving an input from the user, and generating a revised model based upon the input.

18 Claims, 12 Drawing Sheets

(56) References Cited

U.S. PATENT DOCUMENTS

| | | | |
|---|---|---|---|
| 2003/0170889 A1* | 9/2003 | Herron | A61K 49/0008 435/366 |
| 2004/0209234 A1* | 10/2004 | Geiger | G06K 9/4638 434/262 |
| 2006/0013523 A1 | 1/2006 | Childers et al. | |
| 2007/0001879 A1* | 1/2007 | Kaftan | G06K 9/6206 341/79 |
| 2008/0101675 A1* | 5/2008 | Guiliguian | A61B 5/08 382/131 |
| 2008/0212082 A1 | 9/2008 | Froggatt et al. | |
| 2010/0082041 A1 | 4/2010 | Prisco | |
| 2011/0002513 A1* | 1/2011 | Molinari | A61B 6/12 382/128 |
| 2011/0093243 A1* | 4/2011 | Tawhai | G06F 17/5018 703/2 |
| 2012/0041318 A1* | 2/2012 | Taylor | A61B 5/02007 600/504 |
| 2012/0148135 A1* | 6/2012 | Van Rens | G06T 7/143 382/131 |
| 2012/0289777 A1 | 11/2012 | Chopra et al. | |
| 2013/0096377 A1 | 4/2013 | Duindam et al. | |
| 2013/0325493 A1* | 12/2013 | Wong | G16H 50/50 705/2 |
| 2014/0105472 A1* | 4/2014 | Yin | G06T 7/0012 382/128 |
| 2014/0226884 A1* | 8/2014 | Porikli | A61N 5/1037 382/131 |
| 2014/0228860 A1* | 8/2014 | Steines | A61F 2/30942 606/130 |
| 2014/0355858 A1* | 12/2014 | O'Dell | G06T 7/0081 382/131 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SYSTEMS AND METHODS FOR PRE-OPERATIVE MODELING

RELATED APPLICATIONS

This patent application claims priority to and the benefit of the filing date of U.S. Provisional Patent Application 62/048,595, entitled "SYSTEMS AND METHODS FOR PRE-OPERATIVE MODELING," filed Sep. 10, 2014, which is incorporated by reference herein in its entirety.

FIELD

The present disclosure is directed to systems and methods for creating models of a patient's anatomy using a process referred to as segmentation, and more particularly, to systems and methods for segmentation while navigating a patient's anatomy with a medical instrument.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Clinicians may insert medical tools through these natural orifices or incisions to reach a target tissue location. Medical tools include instruments such as therapeutic instruments, diagnostic instruments, and surgical instruments. To reach the target tissue location, a minimally invasive medical tool may navigate natural or surgically created passageways in anatomical systems such as the lungs, the colon, the intestines, the kidneys, the heart, the circulatory system, or the like.

An image guided surgery process typically includes performing some type of pre-operative imaging of a target anatomy of a patient. For example, a Magnetic Resonance Imaging (MRI) image or a Computed Tomography (CT) image may be obtained. Through a manual and/or a computer software-based process, the images are partitioned into segments (e.g., pixels or voxels) that share certain characteristics or computed properties such as color, density, intensity, and texture. This segmentation process results in a two- or three-dimensional reconstruction that forms a model of the target anatomy based on the obtained image. To represent the model, the segmentation process may delineate sets of voxels representing the target anatomy and then apply a function, such as marching cube function, to obtain a 3D surface that encloses the voxels.

Segmentation may be particularly useful in modeling anatomic passageways. After the segmentation process, the obtained model may be used to navigate a medical instrument through the segmented passageways of the patient anatomy. In some cases, various branches within the patient's anatomy may not be properly segmented by the segmentation process. For example, some passageways that exist within the patient anatomy may be omitted from the model. Or, the segmentation process may indicate the existence of branches where there are, in fact, none. Thus, a surgeon or an operator of the medical instrument who is using the model for navigation to a particular anatomic location may be hampered by inaccuracies in the model. To avoid such issues, it is desirable to have an accurate model.

SUMMARY

The embodiments of the invention are summarized by the claims that follow below.

In one example, a method for modeling a patient anatomy includes applying a first modeling function to a set of volumetric image data for a patient anatomy to produce a first model of the patient anatomy, presenting the first model to a user, receiving an input from the user, and generating a revised model based upon the input.

In one example, a computing system includes a user interface, a processor, and a memory that includes machine readable instructions that when executed by the processor, cause the system to, through the user interface, present a first model to a user, the first model being formed by applying a first modeling function to a set of volumetric image data for a patient anatomy to produce a first model of the patient anatomy. The system is further to, through the user interface, receive an input from the user. The system is further to, generate a revised model based upon the input, and present the revised model to the user.

In one example, a method includes, applying a plurality of modeling functions to a set of volumetric image data for a patient anatomy to produce a plurality of models of the patient anatomy, presenting the plurality of models to a user, receiving an input from the user, the input corresponding to an evaluation of the plurality of models, and generating a revised model based upon the input.

In one example, a method includes applying a plurality of modeling functions to a set of volumetric image data for a patient anatomy to produce a plurality of models of the patient anatomy, presenting the plurality of models to a user, receiving an input from the user, the input corresponding to an evaluation of portions of the plurality of models, and generating a revised model based upon the input, the revised model comprising portions from the plurality of models that have a higher evaluation than portions not used in the revised model.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1:
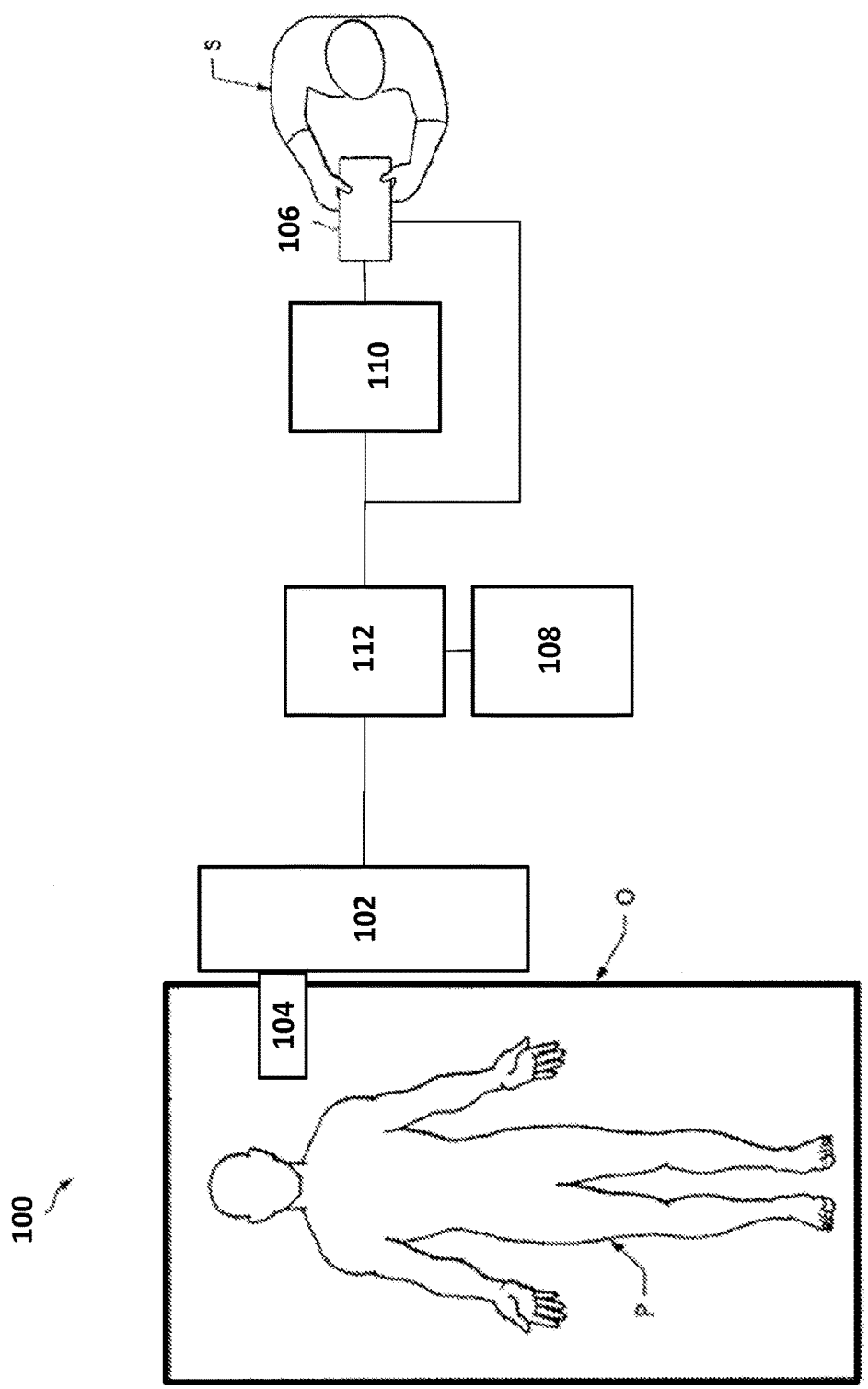
FIG. 1 is a diagram showing an illustrative teleoperational medical system, according to one example of principles described herein.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Referring to FIG. 1 of the drawings, a teleoperational medical system for use in, for example, medical procedures including diagnostic, therapeutic, or surgical procedures, is generally indicated by the reference numeral 100. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures.

As shown in FIG. 1, the teleoperational system 100 generally includes a teleoperational assembly 102 for operating a medical instrument system 104 in performing various procedures on the patient P. The assembly 102 is mounted to or near an operating table O on which a patient P is positioned. The medical instrument system 104 is operably coupled to the teleoperational assembly 102. An operator input system 106 allows a surgeon or other type of clinician S to view images of or representing the surgical site and to control the operation of the medical instrument system 104.

In alternative embodiments, the teleoperational system may include more than one manipulator assembly. The exact number of manipulator assemblies will depend on the surgical procedure and the space constraints within the operating room among other factors.

The operator input system 106 may be located at a surgeon's console, which is usually located in the same room as operating table O. However, it should be understood that the surgeon S can be located in a different room or a completely different building from the patient P. Operator input system 106 generally includes one or more control device(s) for controlling the medical instrument system 104. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of actuators or motors that drive inputs on the medical instrument system 104 in response to commands from the control system (e.g., a control system 112). The motors include drive systems that when coupled to the medical instrument system 104 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 100 also includes a sensor system 108 with one or more sub-systems for receiving information about the instruments of the teleoperational assembly. Such sub-systems may include a position sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The visualization system (e.g., visualization system 231 of FIG. 2) may include a viewing scope assembly (described in greater detail below) such that a concurrent or real-time image of the surgical site is provided to surgeon console. The concurrent image may be, for example, a two or three dimensional image captured by an endoscope positioned within the surgical site. In this embodiment, the visualization system includes endoscopic components that may be integrally or removably coupled to the medical instrument 104. However in alternative embodiments, a separate endoscope, attached to a separate manipulator assembly may be used with the medical instrument to image the surgical site. The visualization system may be implemented as hardware, firmware, software or a combination thereof which interact with or are otherwise executed by one or more computer processors, which may include the processors of a control system 112 (described below).

The teleoperational medical system 100 also includes a display system 110 for displaying an image or representation of the surgical site and medical instrument system(s) 104 generated by sub-systems of the sensor system 108. The display 110 and the operator input system 106 may be oriented so the operator can control the medical instrument system 104 and the operator input system 106 with the perception of telepresence.

The display system 110 may also display an image of the surgical site and medical instruments captured by the visualization system. The display 110 and the control devices may be oriented such that the relative positions of the imaging device in the scope assembly and the medical instruments are similar to the relative positions of the surgeon's eyes and hands so the operator can manipulate the medical instrument 104 and the hand control as if viewing the workspace in substantially true presence. By true presence, it is meant that the presentation of an image is a true perspective image simulating the viewpoint of an operator that is physically manipulating the instrument 104.

Alternatively or additionally, the display 110 may present images of the surgical site recorded and/or modeled preoperatively using imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The presented preoperative images may include two-dimensional, three-dimensional, or four-dimensional images. The presented preoperative or intra-operative images may include two-dimensional, three-dimensional, or four-dimensional (including e.g., time based or velocity based information) images and associated image data sets for reproducing the images.

In some embodiments, the display 110 may display a virtual navigational image in which the actual location of the medical instrument 104 is registered (i.e., dynamically referenced) with preoperative or concurrent images to present the surgeon S with a virtual image of the internal surgical site at the location of the tip of the instrument 104. An image of the tip of the instrument 104 or other graphical or alphanumeric indicators may be superimposed on the virtual image to assist the surgeon controlling the medical instrument. Alternatively, the instrument 104 may not be visible in the virtual image.

In other embodiments, the display 110 may display a virtual navigational image in which the actual location of the medical instrument is registered with preoperative or concurrent images to present the surgeon S with a virtual image of medical instrument within the surgical site from an external viewpoint. An image of a portion of the medical instrument or other graphical or alphanumeric indicators may be superimposed on the virtual image to assist the surgeon controlling the instrument 104.

The teleoperational medical system 100 also includes a control system 112. The control system 112 includes at least one memory and at least one processor (not shown), and typically a plurality of processors, for effecting control between the medical instrument system 104, the operator input system 106, the sensor system 108, and the display system 110. The control system 112 also includes programmed instructions (e.g., a computer-readable medium storing the instructions) to implement some or all of the methods described in accordance with aspects disclosed herein. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The control system 112 may further include a virtual visualization system to provide navigation assistance to the medical instrument system(s) 104. Virtual navigation using the virtual visualization system is based upon reference to an acquired dataset associated with the three dimensional structure of the anatomical passageways. More specifically, the virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software alone or in combination with manual input is used to convert the recorded images into segmented two dimensional or three dimensional composite representation of a partial or an entire anatomical organ or anatomical region. An image data set is associated with the composite representation. The composite representation and the image data set describe the various locations and shapes of the passageways and their connectivity. The images used to generate the composite representation may be recorded preoperatively or intraoperatively during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level tracking images of the patient anatomy and virtual internal images of the patient anatomy. Various systems for using fiber optic sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomical Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated or they may be positioned in separate locations. Multiple operator input systems allow more than one operator to control one or more manipulator assemblies in various combinations.

Figure 2:
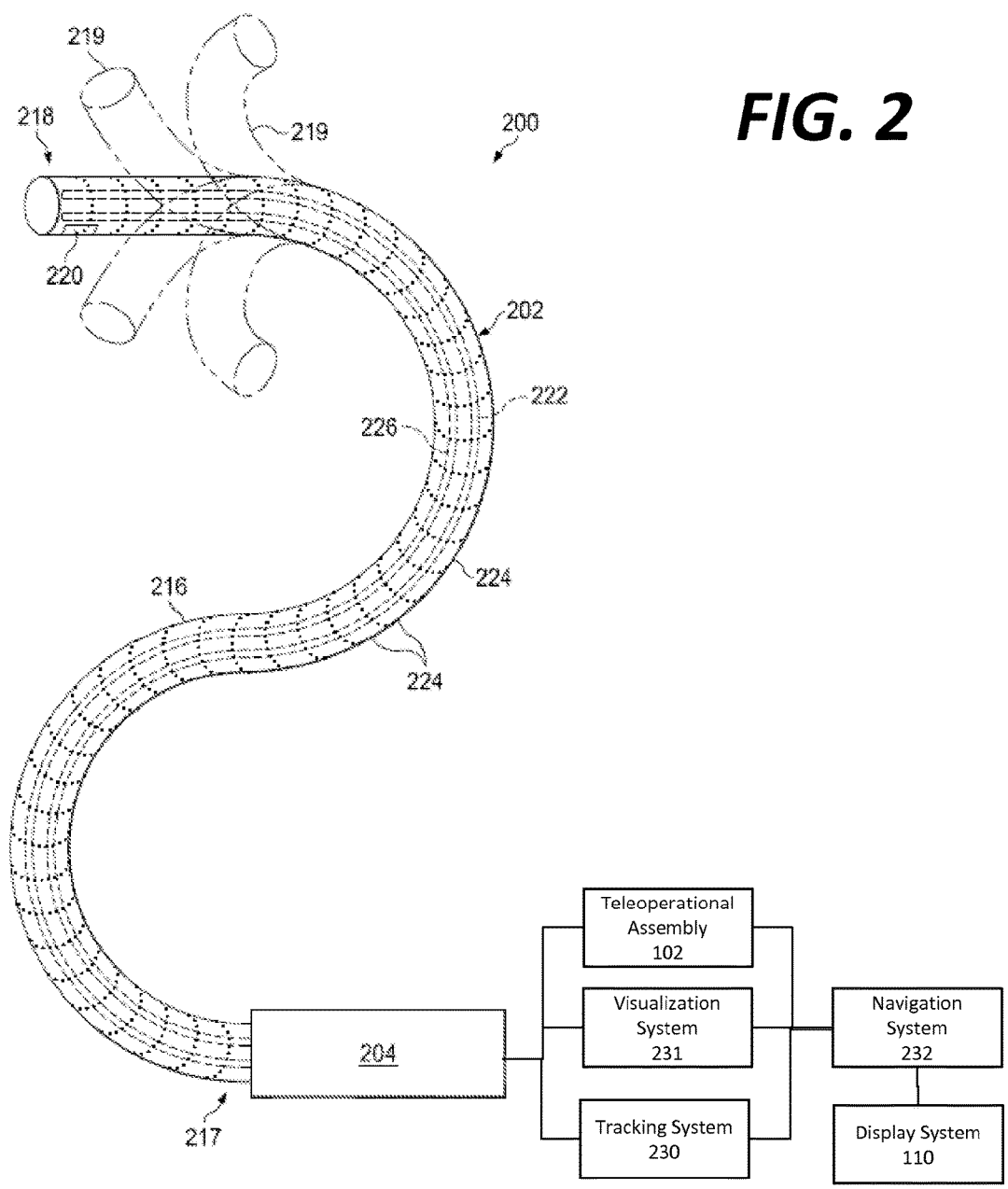
FIG. 2 is a diagram showing an illustrative medical instrument system comprising an endoscopic visualization system, according to one example of principles described herein.

FIG. 2 illustrates a medical instrument system 200, which may be used as the medical instrument system 104 of teleoperational medical system 100. Alternatively, the medical instrument system 200 may be used for non-teleoperational exploratory procedures or in procedures involving traditional manually operated medical instruments, such as endoscopy.

The instrument system 200 includes a catheter system 202 coupled to an instrument body 204. The catheter system 202 includes an elongated flexible catheter body 216 having a proximal end 217 and a distal end or tip portion 218. In one embodiment, the flexible body 216 has an approximately 3 mm outer diameter. Other flexible body outer diameters may be larger or smaller. The catheter system 202 may optionally include a shape sensor 222 for determining the position, orientation, speed, velocity, pose, and/or shape of the catheter tip at distal end 218 and/or of one or more segments 224 along the body 216. The entire length of the body 216, between the distal end 218 and the proximal end 217, may be effectively divided into the segments 224. If the instrument system 200 is a medical instrument system 104 of a teleoperational medical system 100, the shape sensor 222 may be a component of the sensor system 108. If the instrument system 200 is manually operated or otherwise used for non-teleoperational procedures, the shape sensor 222 may be coupled to a tracking system 230 that interrogates the shape sensor and processes the received shape data.

The shape sensor 222 may include an optical fiber aligned with the flexible catheter body 216 (e.g., provided within an interior channel (not shown) or mounted externally). In one embodiment, the optical fiber has a diameter of approximately 200 µm. In other embodiments, the dimensions may be larger or smaller.

The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in alternative embodiments may employ other suitable strain sensing techniques, such as Rayleigh scattering, Raman scattering, Brillouin scattering, and Fluorescence scattering. In other alternative embodiments, the shape of the catheter may be determined using other techniques. For example, the history of the catheter's distal tip pose can be used to reconstruct the shape of the device over the interval of time. As another example, historical pose, position, or orientation data may be stored for a known point of an instrument system along a cycle of alternating motion, such as breathing. This stored data may be used to develop shape information about the catheter. Alternatively, a series of positional sensors, such as EM sensors, positioned along the catheter can be used for shape sensing. Alternatively, a history of data from a positional sensor, such as an EM sensor, on the instrument system during a procedure may be used to represent the shape of the instrument, particularly if an anatomical passageway is generally static. Alternatively, a wireless device with position or orientation controlled by an external magnetic field may be used for shape sensing. The history of the wireless device's position may be used to determine a shape for the navigated passageways.

In this embodiment, the optical fiber may include multiple cores within a single cladding. Each core may be single-mode with sufficient distance and cladding separating the cores such that the light in each core does not interact significantly with the light carried in other cores. In other embodiments, the number of cores may vary, or each core may be contained in a separate optical fiber.

In some embodiments, an array of FBGs is provided within each core. Each FBG comprises a series of modulations of the core's refractive index so as to generate a spatial periodicity in the refraction index. The spacing may be chosen so that the partial reflections from each index change add coherently for a narrow band of wavelengths and therefore reflect only this narrow band of wavelengths while passing through a much broader band. During fabrication of the FBGs, the modulations are spaced by a known distance, thereby causing reflection of a known band of wavelengths. When a strain is induced on the fiber core, however, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBGs produce a reflected wavelength that is a function of the strain on the fiber and its temperature. This FBG technology is commercially available from a variety of sources, such as Smart Fibres Ltd. of Bracknell, England. Use of FBG technology in position sensors for teleoperational surgery is described in U.S. Pat. No. 7,930,065 (filed Jul. 20, 2006) (disclosing "Robotic Surgery System Including Position Sensors Using Fiber Bragg Gratings"), which is incorporated by reference herein in its entirety. The optical fiber may be used to monitor the shape of at least a portion of the catheter system 202. More specifically, light passing through the optical fiber is processed to detect the shape of the catheter system 202 and to utilize that information to assist in surgical procedures. The sensor system (e.g., sensor system 108) may include an interrogation system for generating and detecting the light used for determining the shape of the catheter system 202. This information, in turn, can be used to determine other related variables, such as velocity and acceleration of the parts of a medical instrument system. The sensing may be limited only to the degrees of freedom that are actuated by the teleoperational system, or it may be applied to both passive (e.g., unactuated bending of the rigid members between joints) and active (e.g., actuated movement of the instrument) degrees of freedom.

The medical instrument system may optionally include a position sensor system 220. The position sensor system 220 may be a component of an EM sensor system with the sensor 220 including one or more conductive coils that may be subjected to an externally generated electromagnetic field. Each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

A tracking system 230 may include the position sensor system 220 and a shape sensor system 222 for determining the position, orientation, speed, pose, and/or shape of the distal end 218 and of one or more segments 224 along the instrument 200. The tracking system 230 may be implemented as hardware, firmware, software or a combination thereof which interact with or are otherwise executed by one or more computer processors, which may include the processors of a control system 116.

The flexible catheter body 216 includes a channel sized and shaped to receive an auxiliary instrument 226. Auxiliary instruments may include, for example, image capture probes, biopsy instruments, laser ablation fibers, or other surgical, diagnostic, or therapeutic tools. Auxiliary tools may include end effectors having a single working member such as a scalpel, a blunt blade, an optical fiber, or an electrode. Other end effectors may include, for example, forceps, graspers, scissors, or clip appliers. Examples of electrically activated end effectors include electrosurgical electrodes, transducers, sensors, and the like. In various embodiments, the auxiliary tool 226 may be an image capture probe that includes a distal portion with a stereoscopic or monoscopic camera at or near the distal end 218 of the flexible catheter body 216 for capturing images (including video images) that are processed by a visualization system 231 for display. The image capture probe may include a cable coupled to the camera for transmitting the captured image data. Alternatively, the image capture instrument may be a fiber-optic bundle, such as a fiberscope, that couples to the visualization system. The image capture instrument may be single or multi-spectral, for example capturing image data in one or more of the visible, infrared, or ultraviolet spectrums.

The auxiliary instrument 226 may house cables, linkages, or other actuation controls (not shown) that extend between the proximal and distal ends of the instrument to controllably bend the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The flexible catheter body 216 may also houses cables, linkages, or other steering controls (not shown) that extend between the housing 204 and the distal end 218 to controllably bend the distal end 218 as shown, for example, by the broken dashed line depictions 219 of the distal end. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which the instrument system 200 is actuated by a teleoperational assembly, the housing 204 may include drive inputs that removably couple to and receive power from motorized drive elements of the teleoperational assembly. In embodiments in which the instrument system 200 is manually operated, the housing 204 may include gripping features, manual actuators, or other components for manually controlling the motion of the instrument system. The catheter system may be steerable or, alternatively, the system may be non-steerable with no integrated mechanism for operator control of the instrument bending. Also or alternatively, one or more lumens, through which medical instruments can be deployed and used at a target surgical location, are defined in the walls of the flexible body 216.

In various embodiments, the medical instrument system 200 may include a flexible bronchial instrument, such as a bronchoscope or bronchial catheter, for use in examination, diagnosis, biopsy, or treatment of a lung. The system 200 is also suited for navigation and treatment of other tissues, via natural or surgically created connected passageways, in any of a variety of anatomical systems, including the colon, the intestines, the kidneys, the brain, the heart, the circulatory system, and the like.

The information from the tracking system 230 may be sent to a navigation system 232 where it is combined with information from the visualization system 231 and/or the preoperatively obtained models to provide the surgeon or other operator with real-time position information on the display system 110 for use in the control of the instrument 200. The control system 116 may utilize the position information as feedback for positioning the instrument 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety.

In the embodiment of FIG. 2, the instrument 200 is teleoperated within the teleoperational medical system 100. In an alternative embodiment, the teleoperational assembly 102 may be replaced by direct operator control. In the direct operation alternative, various handles and operator interfaces may be included for hand-held operation of the instrument.

Figure 3:
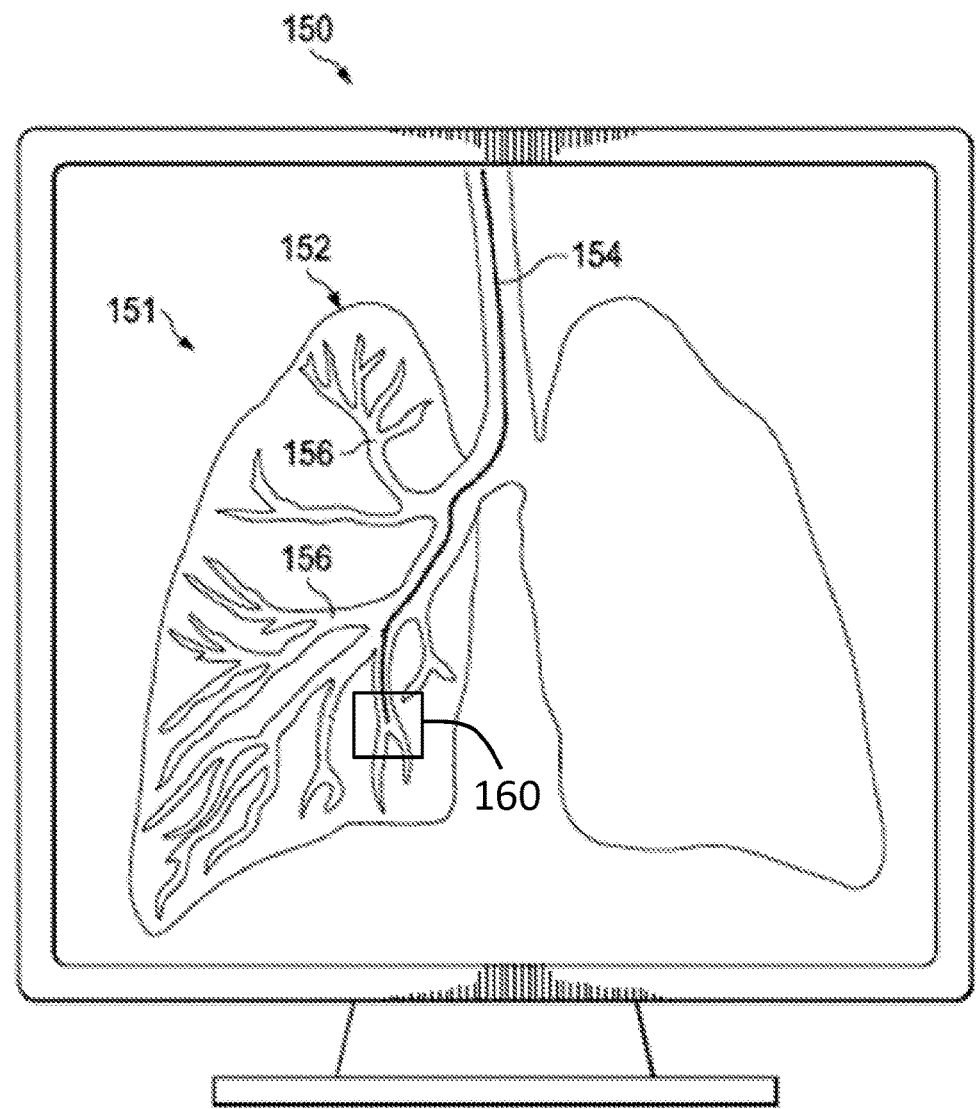
FIG. 3 is a diagram showing a model patient anatomy, according to one example of principles described herein.

FIG. 3 depicts a composite image 150 including a model 151 of a human lung 152, from a viewpoint external to the lung. The model lung 151 is registered with an instrument image 154 of a flexible instrument, such as catheter system 202. The model 151 of the lung 152 may be generated from a set of scanned images (e.g., pre-operative CT or MRI images) using a modeling function such as a segmentation process. The composite image 150 may be displayed via display system 110. As the instrument is advanced through bronchial passageways 156 of the lung 152, information from the tracking system 230 and/or the visualization system 231 is used to register the instrument image 154 with the model lung image 151. The view of the model 151 of the lung 152 may change, for example, to depict the lung in a state of inspiration or expiration. The instrument image 154 may change to depict the advancement or withdrawal of the instrument through the bronchial passageways 156. In some examples, the model 151 may also include a target region 160. The target region 160 may represent a destination for the surgical instrument. For example, when performing a biopsy, the tissue to be extracted is within the target region 160. Thus, the surgeon can use the model 151 to plan a route for the instrument to reach the target region 160.

Figure 4B:
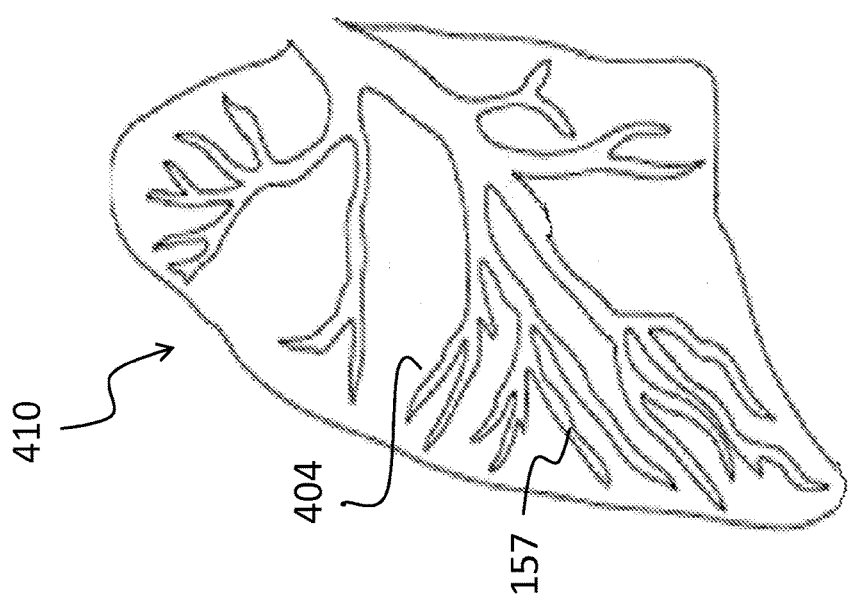
FIG. 4B is a diagram showing an illustrative model anatomy of the target anatomy, according to one example of principles described herein.
Figure 4A:
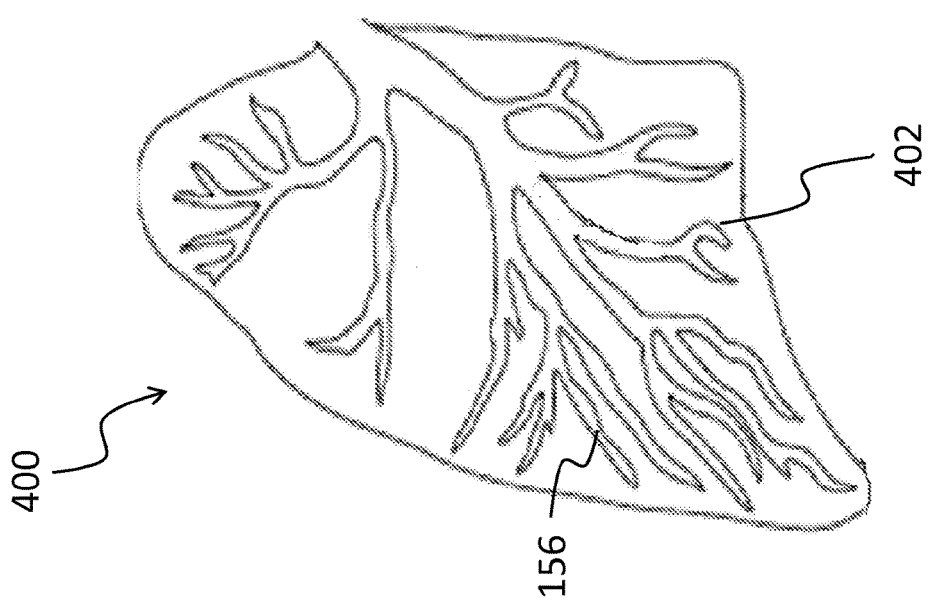
FIG. 4A is a diagram showing an illustrative target anatomy, according to one example of principles described herein.

FIG. 4a is a diagram showing an illustrative target anatomy 400, particularly, a patient's lung. The anatomy 400 represents the actual patient's lung, including all real branches and bronchial passages 156. FIG. 4b is a diagram showing an illustrative model anatomy 410 of the target anatomy. The model 410 is created through a modeling process such as a segmentation process in which a composite of the scanned images is partitioned into segments (e.g., pixels or voxels) that correspond to some anatomical structure (e.g. airway, bronchial wall, parenchyma, etc.) on the basis of appearance such as intensity or texture. This segmentation process results in a two- or three-dimensional reconstruction that forms the model 410. To represent the model, the segmentation process may delineate sets of voxels representing the target anatomy and then apply a function, such as marching cube function, to obtain a 3D surface that encloses the voxels.

Figure 5:
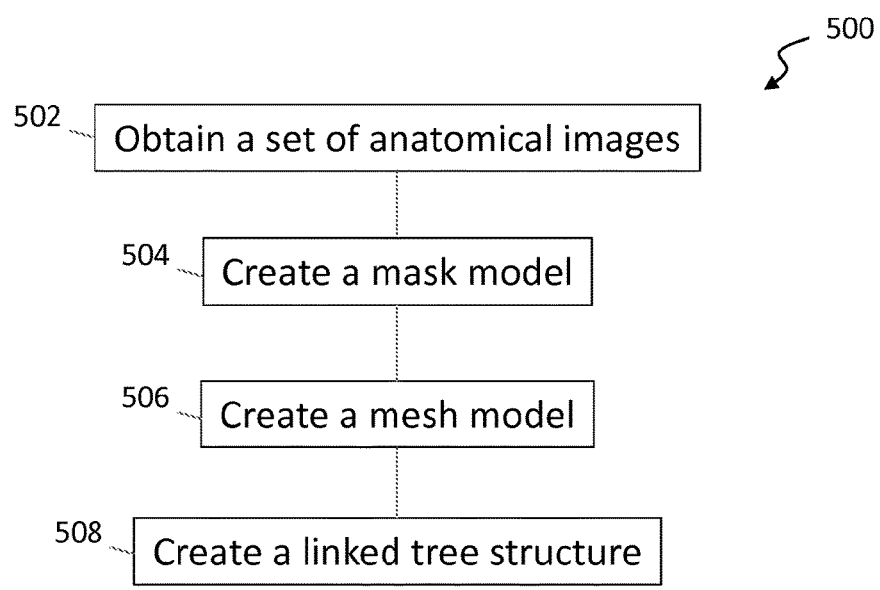
FIG. 5 is a flowchart showing an illustrative method for anatomic segmentation, according to one example of principles described herein.

In one particular example, as shown in FIG. 5, a segmentation method 500 includes a process 502 of obtaining a set of anatomical images such as from a patient CT or MRI scan. At a process 504, a mask model is created from the three-dimensional compilation of the set of anatomical images. For example, the anatomical passageways may be distinguished from surrounding tissue by assigning a first value (e.g., 1) to the airways and a second value (e.g., 0) to the surrounding tissue. If a particular region cannot be definitively determined to be a passageway or a region of surrounding tissue, a probabilistic value (e.g., something other than a 1 or 0) may be assigned to the indeterminate region. This can help a clinician to decide how to combine multiple segmentation functions by considering the probabilistic value of each of the branches or airways. At a process 506, a mesh model may be created of the segmented passageways. Further details of the creation of a mesh model are described in detail in U.S. Provisional Patent Appl. No. 61/935,547 (filed on Feb. 4, 2014) (disclosing "Systems and Methods for Non-rigid Deformation of Tissue for Virtual Navigation of Interventional Tools") which is incorporated by reference herein in its entirety. At a process 508, a linked tree structure may be generated from the mesh model as described in further detail in U.S. Provisional Patent Appl. No. 61/935,547.

Ideally, the bronchial passages 157 within the model 410 will match the actual bronchial passages 156 of the patient anatomy 400. But, conventional segmentation processes used to create the model 410 may not create a model that accurately matches the actual anatomy. For example, the segmentation function may create a model having an additional passageway 404 that is not in the actual anatomy 400. In reliance upon this incorrect information, the clinician or an automated navigation system may plan a procedure that requires the medical instrument to navigate through or to the non-existent passageway to reach a target tissue. When the clinician reaches the location of the modeled passageway 404 and finds that, in fact, no passageway exists, the clinician may have to plan another approach to the target tissue. In some cases, the segmentation process may fail to render a passageway 402 that exists within the actual anatomy. In reliance upon this incorrect information, the clinician or an automated navigation system may not be able to plan the most effective route for a medical instrument to navigate to reach a target tissue.

Figure 6A:
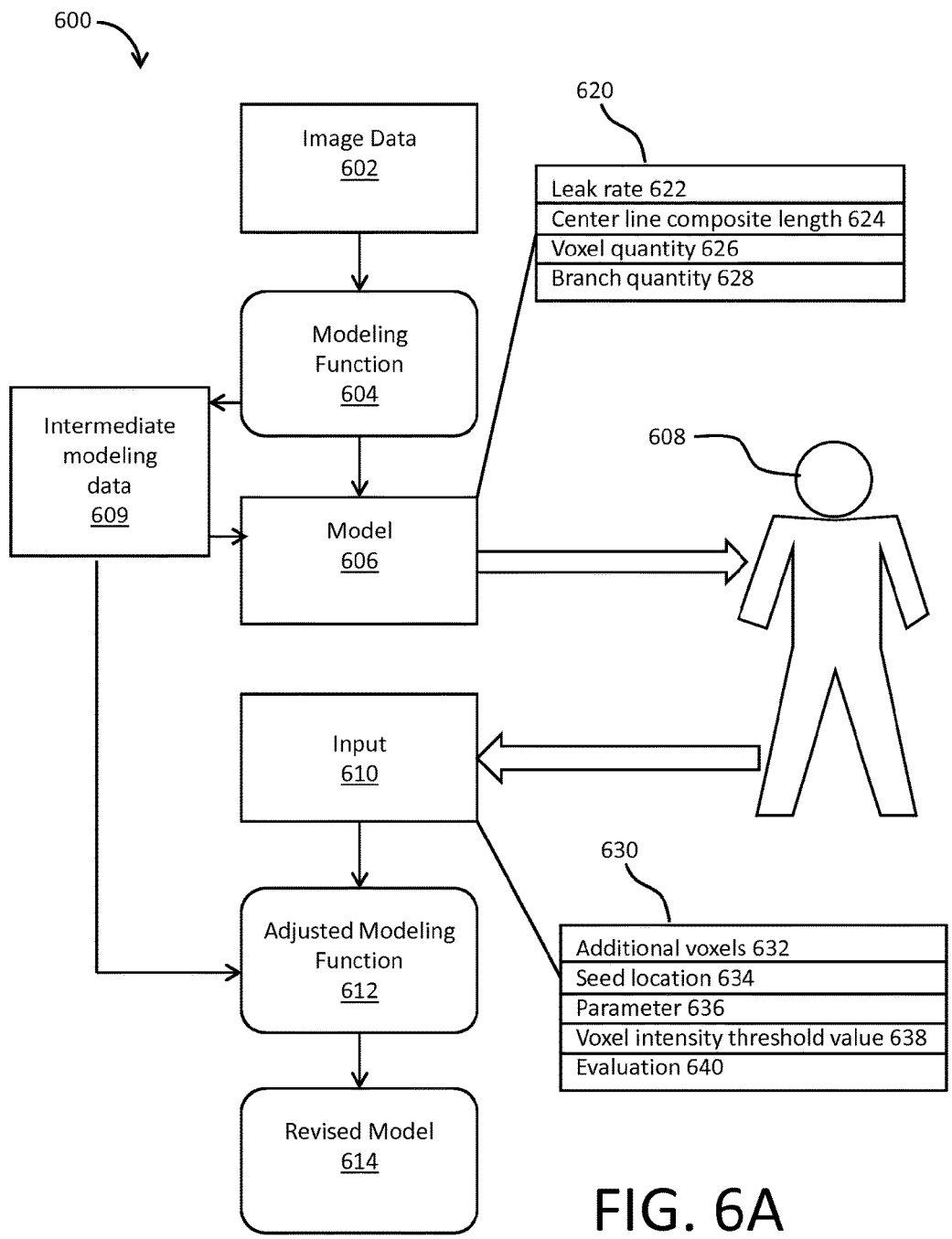
FIGS. 6a and 6b are block diagrams showing illustrative pre-operative segmentation techniques, according to one example of principles described herein.
Figure 6B:
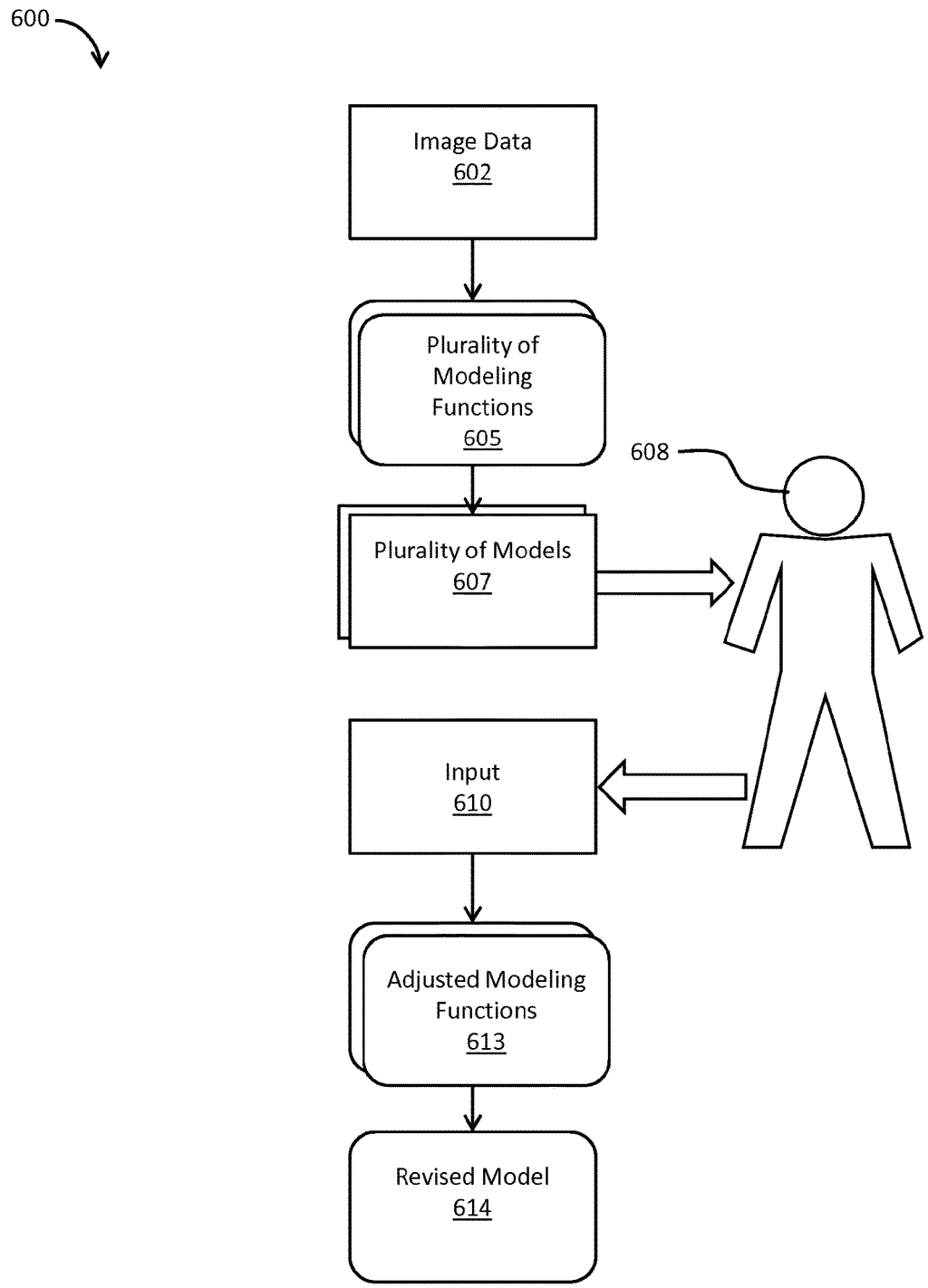

FIGS. 6a and 6b are block diagrams showing illustrative pre-operative segmentation techniques 600. According to the present example, image data 602 from images of a patient's anatomy is obtained. The image data 602 may be in the form of volumetric image data. Images of the patient's anatomy may be taken through various scanning techniques such as X-ray, CT scans, or MRI scans.

A modeling function 604 is then used to create a model 606 of the patient's anatomy using the image data 602. For example, the modeling function 604 may include a segmentation process as described above. Different segmentation functions may produce different models with varying features. For example, some segmentation functions may be better at detecting straight bronchial passageways while other segmentation functions are better at detecting curved bronchial passageways. Additionally, some segmentation functions may be better at distinguishing between bronchial passageways and pulmonary arteries that parallel those bronchial passageways. A particular modeling function 604 may be associated with a number of parameters 620, including leak rate 622, center line composite length 624, voxel quantity 626, and branch quantity 628.

The leak rate 622 is a measurement of the number of additional passageways within a model 606 that do not correspond to actual passageways within the patient's anatomy. Specifically, a more aggressive segmentation function may have a higher leak rate. Thus, the model constructed from such a segmentation function may indicate that there are several branches where there are in fact none. A higher leak rate may be acceptable and even beneficial in some cases. For example, a segmentation function with a higher leak rate may be useful for patient's having certain conditions such as pneumonia or other pathological conditions that cause the anatomic passageways to become ambiguous. In some cases, however, a lower leak rate may be beneficial for patients having certain pathological conditions or to generally avoid erroneous passageway identification.

Determination of the leak rate 622 may involve an experienced clinician making a manual comparison of patient images and models constructed from those images using various segmentation functions. Specifically, an experienced clinician may be able to view the patient images and determine which branches within the model correspond to actual bronchial passageways and which branches do not correspond to actual bronchial passageways. Segmentation functions that tend to create additional bronchial passageways may be defined as having a higher leak rate 622. Alternatively, the leak rate for a segmentation function may be determined by a calibration process in which each segmentation function is compared to a predetermined ideal result.

The center line composite length 624 is a composite number based on the length of all the segmented passageways. In one example, the composite number is the sum of all the lengths. The center line composite length 624 thus indicates the magnitude of the passageways that were segmented. A larger center line composite length 624 indicates more segmented passageways. A large center line composite length may indicate a more aggressive segmentation function than a segmentation function that produces a shorter center line composite length. A clinician may use the center line composite length 624 to choose an appropriately aggressive segmentation function. For example, if a patient has a condition that prevents a generally good segmentation function from segmenting much of the lung, the center line composite length may encourage the clinician to choose a more aggressive starting point for the segmentation function.

The voxel quantity 626 indicates the number of voxels that were segmented. A voxel is a volume element. A model 606 with a higher quantity of voxels will generally have larger or longer passageways. Thus, voxel quantity gives an idea of the overall volume of passageways within the model 606. A higher voxel quantity may indicate a more aggressive segmentation function than segmentation function that produces a lower voxel quantity. A clinician may use the voxel quantity 626 to choose an appropriately aggressive segmentation function.

Branch quantity 628 indicates the total number of branches that were segmented to create the model 606. A model 606 with a higher number of branches may indicate that the anatomy itself has more branches, or the model was created with a modeling function having a higher leak rate, thus creating additional branches that do not correspond to actual branches. A greater number of branches may indicate a more aggressive segmentation function than a segmentation function that produces a lower voxel quantity. A clinician may use the branch quantity 628 to choose an appropriately aggressive segmentation function.

After the model 606 has been constructed, it is presented to a user 608. The user may be a doctor, surgeon, or clinician. The user 608 can then evaluate the model and determine if it should be revised. Specifically, the user 608 may compare the model to scanned images of a patient's anatomy from which the model 606 was derived. The user thus provides input 610 to create an adjusted modeling function 612. The adjusted modeling function 612 is then used to create a revised model 614. This process may be repeated. Specifically, the user 608 may view the revised model 614, provide further input to create a further adjusted modeling function, and create a further revised model. The input 610 provided by the user 608 may include a number of input elements 630 including, but not limited to, additional voxels 632, seed locations 634, an aggressiveness parameter 636, a voxel intensity threshold value 638, and an evaluation 640.

In one example, the user 608 can manually add additional voxels 632 to the model 606. This may be done to add a branch that was not found by the segmentation function. Alternatively, this may be done to widen a passageway that was constructed too narrowly by the modeling function 604. After receiving such input 610, the adjusted modeling function 612 may segment branches extending from a main branch to which voxels were added by the user 608. Based on the changes made by the user 608, the extending branches may be segmented differently than they were before the user added voxels to the main branch manually.

In one example, the user 608 can manually add seed locations 634 to the model 606. Seed locations 634 instruct the adjusted modeling function 612 to focus on a particular spot. For example, a seed location 634 may be used to indicate a location of a missed branch. Thus, the adjusted modeling function 612 can focus a more aggressive or detailed segmentation analysis on area of the identified seed location 634 when creating the revised model 614. By focusing more on that area, the missing branch is more likely to be segmented properly in the revised model 614. In another aspect, the seeds may serve as hints, forcing the model segmentation analysis to extend the model so as to include the newly added seeds.

In one example, the user 608 can manually change or tune a parameter 636 that modifies the segmentation analysis. In one example, the parameter may be an indication of aggressiveness, inclusiveness, or another factor that will increase or diminish segmentation. Other types of parameters are contemplated as well. It may be the case that the user 608 notices that several branches within the real patient anatomy were missed by the modeling function 604. The user 608 may also determine that a different parameter 636, such as a more inclusive parameter, would solve that issue. In some cases, the user 608 may determine that there are too many extraneous branches within the model 606 that do not correspond to real branches within the patient's anatomy. Therefore, the user 608 may elect a different parameter 636, such as a less inclusive parameter.

In one example, the input 610 may include a voxel intensity threshold value 638. Each voxel may be assigned an intensity value based on the portion of the image data corresponding to that voxel. The intensity value may be based on a color metric or a grayscale metric. The intensity value can be used to define whether the voxel represents a passageway or something else. For example, in the lung, different intensity values may distinguish bronchial passageways from arterial passageways and other human tissue. The user 608 may change the voxel intensity threshold to change how the adjusted modeling function 612 classifies a voxel as being either part of a passageway or something else. In one example, raising the voxel intensity threshold value 638 causes the adjusted modeling function to find fewer branches. This may be desirable if the model 606 has a relatively high leak rate. Conversely, lowering the voxel intensity threshold value 638 may cause the adjusted modeling function 612 to find additional branches.

In one example, the input 610 includes evaluations. Evaluations may be any type of indication as to the effectiveness of the modeling function. For example, the user 608 can indicate that segmentation was done well in a particular area and not done sufficiently in another area. This can allow the adjusted modeling function 612 to find other areas in the patient image data that are similar to the areas that were indicated as being segmented well. It can then be inferred that similar areas were also segmented well. The adjusted modeling function 612 can then make further changes in areas that were not indicated as being segmented well.

In some examples, a modeling function 604 may store intermediate modeling data 609. Intermediate modeling data 609 may be data in any state between the image data 602 and the model 606. It may be the case that a modeling function 604 utilizes a substantial amount of processing resources. Thus, it may be useful to have intermediate modeling data 609 that does not have to be reprocessed by the adjusted modeling function 612. Intermediate modeling data may include distance metrics, spatial filtering outputs, or morphological filtering. For example, the modeling function 604 may create a main branch and several smaller branches extending from the main branch. The input 610 may indicate that further processing is to be performed on only one of the smaller branches. Thus, the adjusted modeling function 612 can use the intermediate modeling data 609 for the main branch and other smaller branches that are unrelated to the input 610.

In some examples, the processing of image data 602 may be performed by a cloud computing system. The intermediate modeling data 609 may also be stored in the cloud computing system. In some examples, the processing of image data 602 may be performed by a local computing system that is not necessarily connected to a network.

Other types of intermediate modeling data 609 are contemplated. For example, the modeling function 604 may process the image data 602 into various formats to allow for easy use by various processes associated with the modeling function. The adjusted modeling function may use this specially formatted data rather than having to reformat that data from the image data 602.

FIG. 6b illustrates additional pre-operative modeling techniques. According to the present example, a plurality of modeling functions 605 is used to create a plurality of models 607 to be presented to a user 608. The user may then provide input 610 on one or more of those models 607. For example, the user may evaluate the accuracy of each of the models and provide such evaluations as input 610. The user may provide various input 610 as described above for each of the plurality of models 607. The input 610 may then be used by adjusted modeling functions 613 that are used to create a revised model 614. The revised model 614 may be the model used during a surgical procedure.

Figure 7:
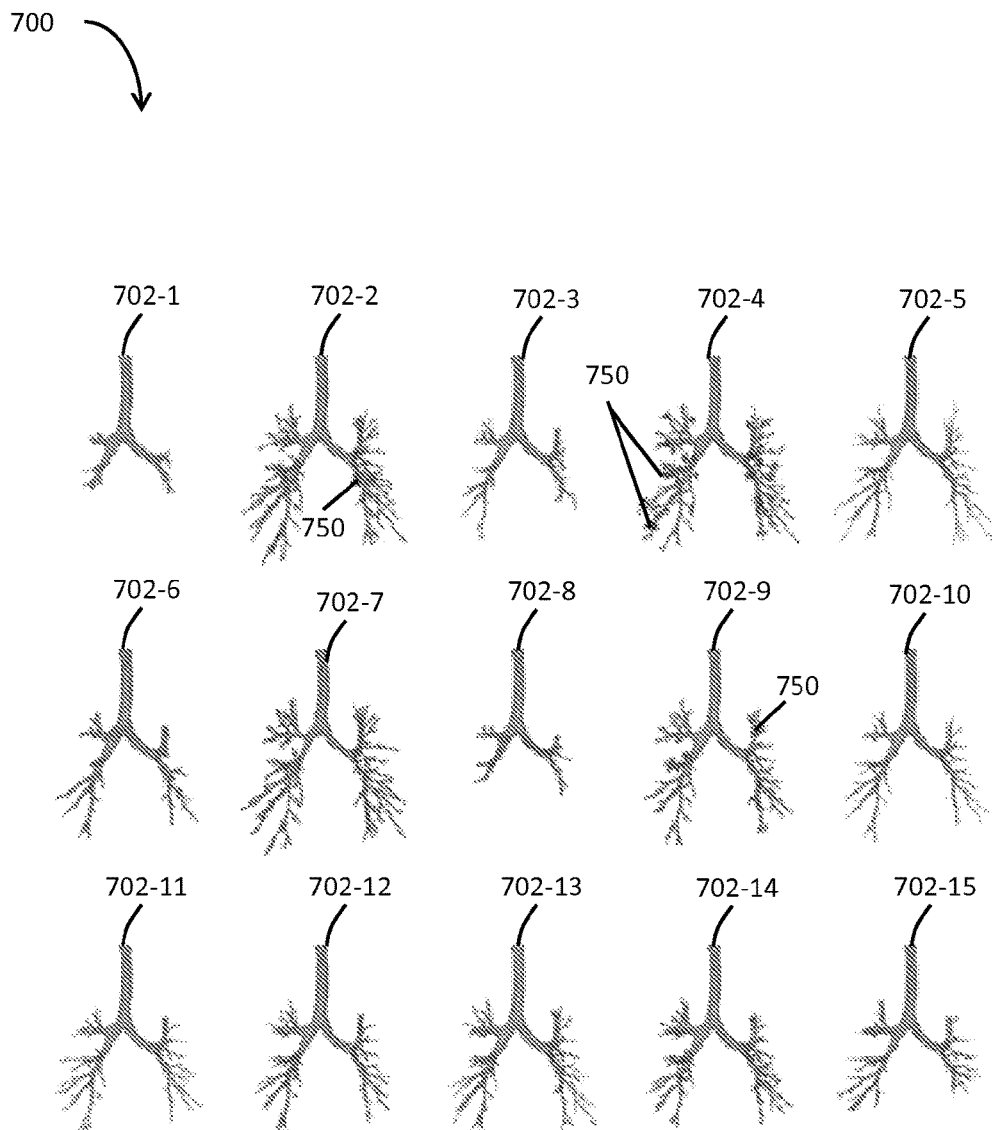
FIG. 7 is a diagram showing a set of a plurality of models derived from patient image data, according to one example of principles described herein.

FIG. 7 is a diagram 700 showing a set of a plurality of models derived from patient image data. According to the present example, each of the models 702 that are illustrated is derived from a different modeling function. Some models 702-2, 702-4, 702-7, 702-9, 702-14 have a higher leak rate as indicated by leakage shading 750. Such models may have been created by a more aggressive modeling function. Some models 702-1, 702-8 have a relatively small number of bronchial passageways. Such models are typically created by more conservative modeling functions. The remaining models 702-3, 702-5, 702-6, 702-10, 702-11, 702-12, 702-13, 702-15 have varying characteristics. Some models 702 have more branches than others, and some models have wider passageways than others.

A user can view such models to determine which model most accurately resembles the actual patient anatomy. In some cases, however, the user may determine that various models should be combined in various manners to form a final model. Examples of such combinations are discussed below.

Figure 8:
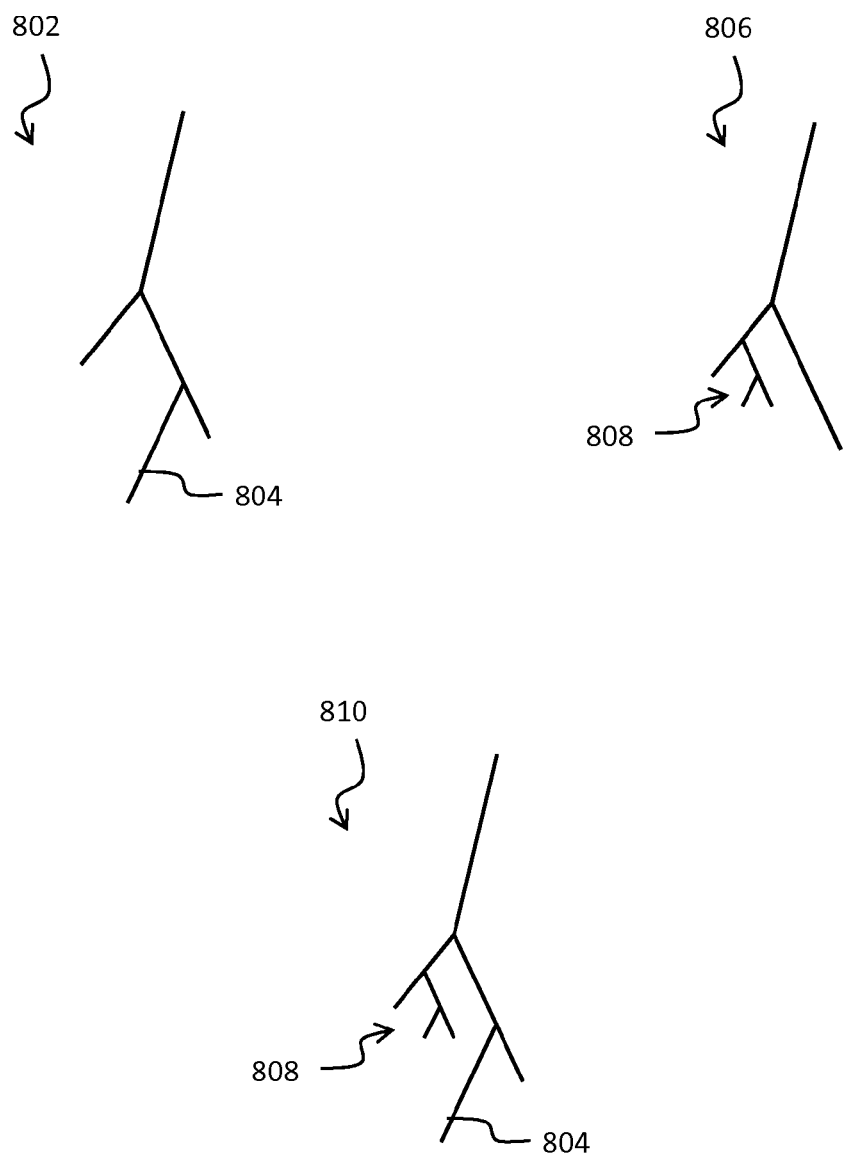
FIG. 8 is a diagram showing an illustrative union of two models, according to one example of principles described herein.

FIG. 8 is a diagram showing an illustrative union of two models. According to the present example, a user may be presented with both a first model 802 and a second model 806. Both models 802, 806 may have been created using different modeling functions. The user may decide that a union of the models 802, 806 would produce a more accurate final model. For example, the modeling function for the first model 802 found branch 804, but the modeling function for the second model 806 did not find that branch. Additionally, the modeling function for the second model 806 found portion 808, but the modeling function for the first model 802 did not find that portion. Thus, the union of the two models produces a revised model 810 that includes both portion 808 and branch 804.

Figure 9:
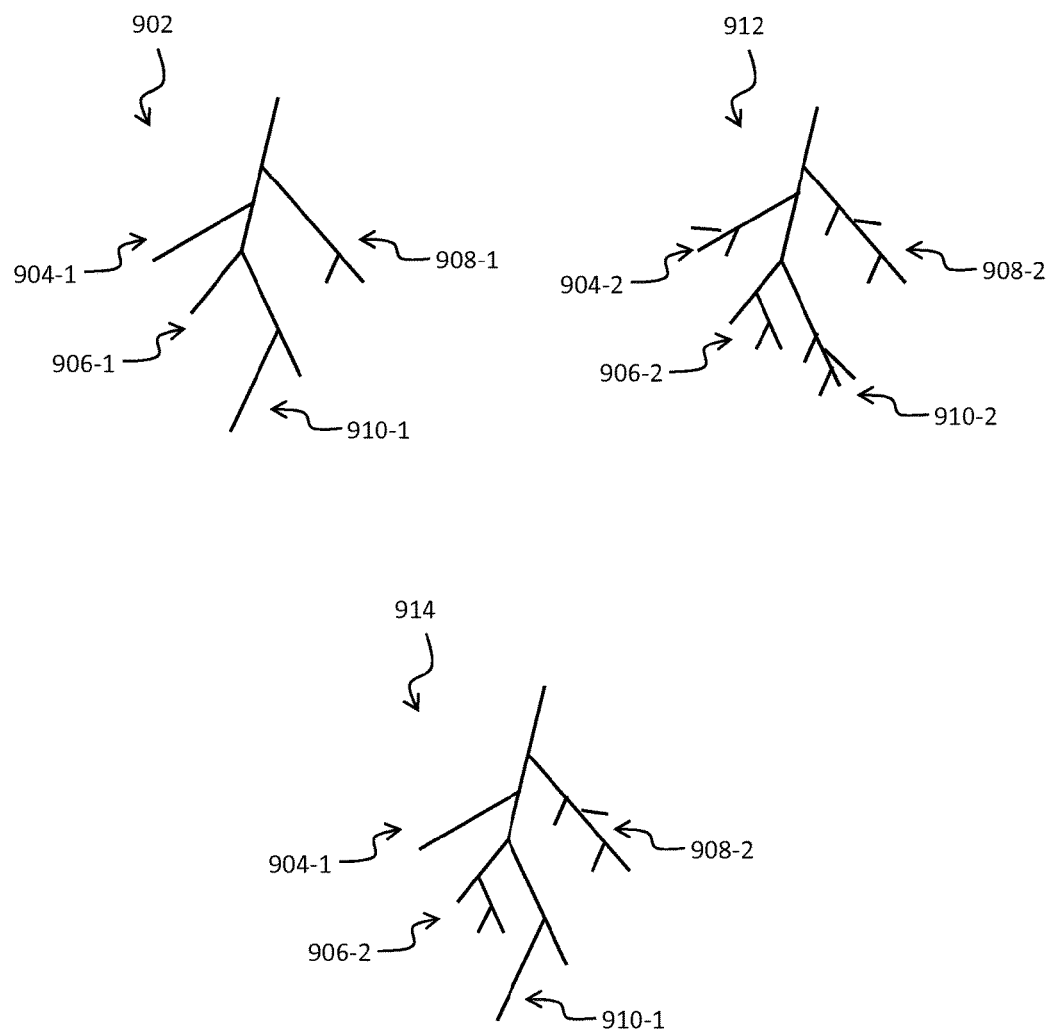
FIG. 9 is a diagram showing an illustrative combination of sub-portions of a plurality of combinations, according to one example of principles described herein.

FIG. 9 is a diagram showing an illustrative combination of sub-portions of a plurality of combinations. In some cases, a user may wish to select various portions from one model and different portions from another model. In the present example, a first model 902 created with a first modeling function includes a number of sub-portions 904-1, 906-1, 908-1, 910-1. Additionally, a second model 912 created with a second modeling function includes a number of sub-portions 904-2, 906-2, 908-2, 910-2.

A user may decide that some portions from the first model 902 are more accurate and some portions from the second model 912 are more accurate. Thus, the user can combine different portions to form a revised model 914. Specifically, the revised model 914 includes sub-portions 904-1 and 910-1 from the first model 902 and sub-portions 906-2 and 908-2 from the second model 912.

Figure 10:
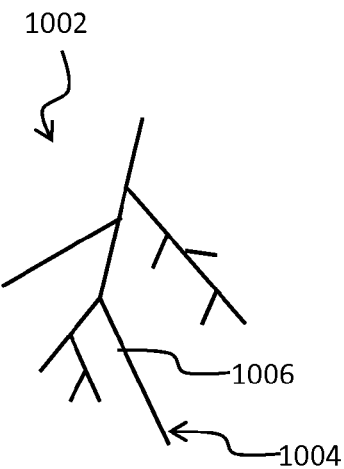
FIG. 10 is a diagram showing a sub-portion of a model being revised, according to one example of principles described herein.
Figure 10:
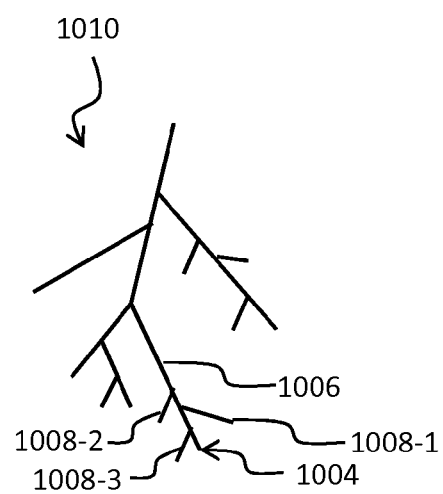

FIG. 10 is a diagram showing a sub-portion of a model being revised. According to the present example, a user may wish to adjust a modeling parameter for a particular sub-portion 1004 of the model 1002. It may be the case that that particular sub-portion includes a target region as described above. Thus, the user may not be concerned with the accuracy of other portions of the model. For a model of branching airways, such as a linked airway tree, any sub-portion may be automatically exchanged or sub-processed based on selection of links by a user. Similarly, larger airway portions, such as a hierarchy of airway links may also be exchanged or sub-processed, based on connections between a selected airway link and other airway links or a target region. Generally, associating voxels with specific airways allows for efficient portion exchange and editing of multiple models.

The revised model 1010 is the same as the original model 1002, except for the changes made to the selected sub-portion 1004. While the original sub-portion 1004 included a single branch, the revised sub-portion 1004 includes a number of smaller branches 1008-1, 1008-2, 1008-3 that extend from the main branch. The additional branches 1008-1, 1008-2, 1008-3 may be the result of a segmentation function with one or more different parameters. As described above, different parameters may cause more branches to be found.

Figure 11:
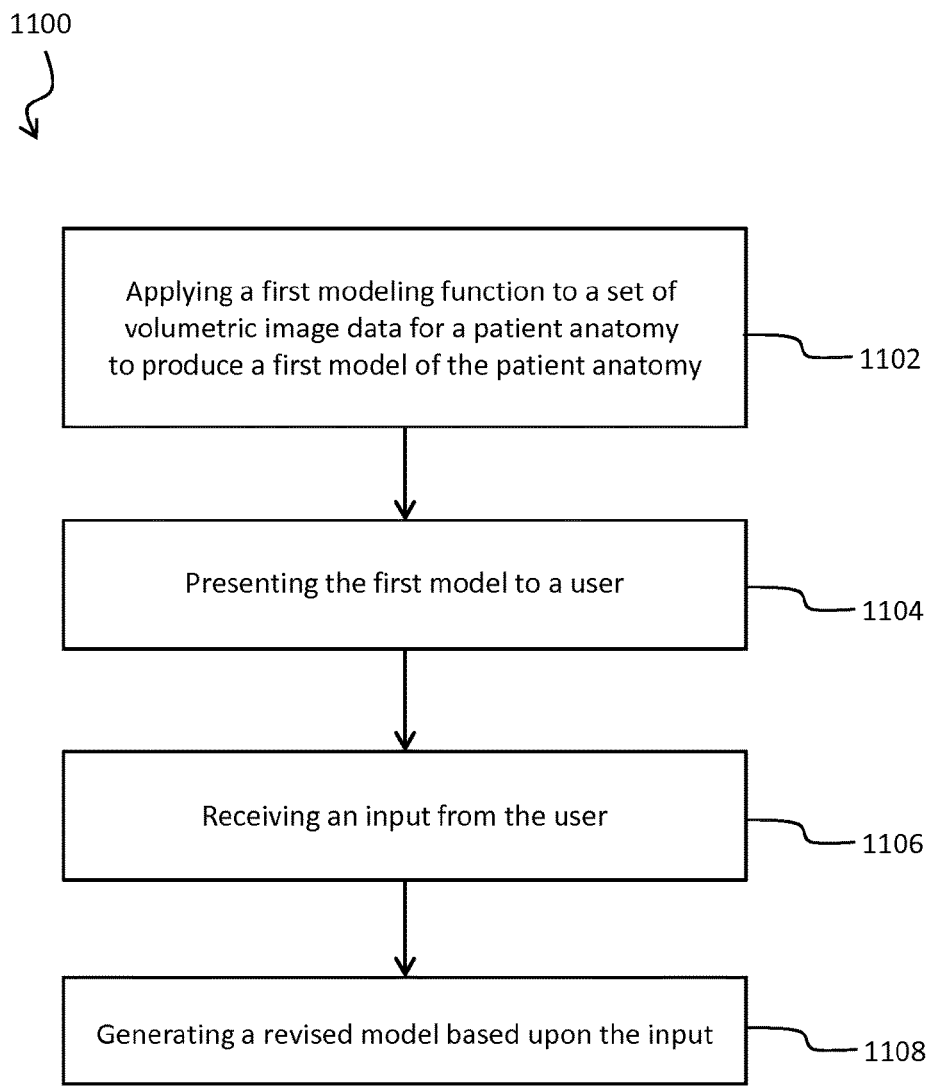
FIG. 11 is a flowchart showing an illustrative method for pre-operative modeling techniques, according to one example of principles described herein.

FIG. 11 is a flowchart showing an illustrative method 1100 for pre-operative modeling techniques. According to the present example, the method 1100 includes a process 1102 for applying a first modeling function to a set of volumetric image data for a patient anatomy to produce a first model of the patient anatomy. A process 1104 includes presenting the first model to a user. A process 1106 includes receiving an input from the user. A process 1108 includes generating a revised model based upon the input. The processes described above may be repeated until a user is satisfied with the revised model. The revised model can then be used as a model for a surgical operation.

The systems and methods of this disclosure may be used for connected bronchial passageways of the lung. The systems and methods may also be suited for navigation and treatment of other tissues, via natural or surgically created connected passageways, in any of a variety of anatomical systems including the colon, the intestines, the kidneys, the brain, the heart, the circulatory system, or the like. The methods and embodiments of this disclosure are also suitable for non-surgical applications.

One or more elements in embodiments of the invention may be implemented in software to execute on a processor of a computer system such as control processing system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A computing system comprising:
    a user interface;
    a processor; and
    a memory comprising machine readable instructions that when executed by the processor, cause the system to:
    through the user interface, present a patient-specific model of a patient anatomy to a user, the patient-specific model being formed by applying a first segmentation function to a set of volumetric image data for the patient anatomy to produce the patient-specific model of the patient anatomy;
    through the user interface, receive an input from the user;
    generate a revised model by applying an adjusted segmentation function to the set of volumetric image data, the adjusted segmentation function based upon the input; and
    present the revised model to the user,
    wherein the patient-specific model is associated with a plurality of patient-specific model parameters, wherein the plurality of patient-specific model parameters includes a leak rate, the leak rate being a measurement of additional passageways within the patient-specific model that do not correspond to actual passageways within the patient anatomy.

2. The system of claim 1 wherein the plurality of patient-specific model parameters includes a center line composite length.

3. The system of claim 1 wherein the plurality of patient-specific model parameters includes a quantity of voxels in the patient-specific model.

4. The system of claim 1 wherein the plurality of patient-specific model parameters includes a quantity of branches in the patient-specific model.

5. The system of claim 1 wherein the input received from the user includes additional voxels representing additional features of the patient anatomy.

6. The system of claim 1 wherein the input received from the user includes a seed location and to generate the revised model, the processor is further to cause the system to apply a second segmentation function to the set of volumetric image data in a region of the seed location.

7. The system of claim 1 wherein the input received from the user includes a tunable parameter for at least a portion of the patient-specific model and to generate the revised model, the processor is further to cause the system to reapply the first segmentation function with different parameters.

8. The system of claim 1 wherein the input received from the user includes identification of a route to a target region.

9. The system of claim 8 wherein the input received from the user includes identification of vasculature proximate to the route to the target region.

10. The system of claim 1 wherein the input received from the user includes a threshold voxel intensity value and to generate the revised model, the processor is further to cause the system to omit voxels with a voxel intensity less than the threshold voxel intensity value.

11. The system of claim 1, wherein the processor is further to cause the system to:
    apply a plurality of segmentation functions to the set of volumetric image data for the patient anatomy to produce a plurality of models of the patient anatomy, wherein the first segmentation function is one of the plurality of segmentation functions and the patient-specific model is one of the plurality of models; and
    present the plurality of models to the user.

12. The system of claim 11, wherein the input received from the user is an evaluation of the plurality of models.

13. The system of claim 12, wherein generating the revised model includes combining sub-portions of at least two of the plurality of models.

14. The system of claim 13 wherein the input received from the user includes identification of the sub-portions of the at least two of the plurality of models.

15. The system of claim 13, wherein the sub-portions of the models are mixed based on at least one of: a selected airway link or airway links connected to the selected link.

16. The system of claim 12 wherein to apply the plurality of segmentation functions to the set of volumetric data for the patient anatomy, the processor is further to cause the system to generate a set of intermediate modeling data for each of the plurality of segmentation functions and generating the revised model includes applying the input to the intermediate modeling data.

17. The system of claim 16 wherein the intermediate modeling data is associated with a subset of the set of volumetric image data.

18. The system of claim 1, wherein the patient-specific model includes a plurality of regions, each region having a probabilistic value indicating a probability that that region is a passageway in the patient anatomy.

\* \* \* \* \*